United States Patent [19]

Caruso

[11] Patent Number: 5,891,885
[45] Date of Patent: *Apr. 6, 1999

[54] METHOD FOR TREATING MIGRAINE

[75] Inventor: Frank S. Caruso, Colts Neck, N.J.

[73] Assignee: Algos Pharmaceutical Corporation, Neptune, N.J.

[ * ] Notice: This patent issued on a continued prosecution application filed under 37 CFR 1.53(d), and is subject to the twenty year patent term provisions of 35 U.S.C. 154(a)(2).

[21] Appl. No.: 736,370

[22] Filed: Oct. 24, 1996

Related U.S. Application Data

[63] Continuation-in-part of Ser. No. 727,923, Oct. 9, 1996, abandoned.

[51] Int. Cl.⁶ .................... A61K 31/44; A61K 31/405; A61K 31/13
[52] U.S. Cl. .................... 514/289; 514/415; 514/661; 514/662
[58] Field of Search .................... 514/415, 289, 514/662, 661

[56] References Cited

U.S. PATENT DOCUMENTS

| | | |
|---|---|---|
| 4,650,810 | 3/1987 | Bays et al. . |
| 4,914,125 | 4/1990 | Baldinger et al. . |
| 4,916,125 | 4/1990 | Herrling et al. . |
| 4,994,484 | 2/1991 | Binder et al. . |
| 5,021,428 | 6/1991 | Carr et al. . |
| 5,155,218 | 10/1992 | Weinshank et al. .................... 536/27 |
| 5,200,413 | 4/1993 | King et al. . |
| 5,242,949 | 9/1993 | Goldberg et al. . |
| 5,248,684 | 9/1993 | Suzuki et al. . |
| 5,273,759 | 12/1993 | Simmons . |
| 5,317,103 | 5/1994 | Baker et al. . |
| 5,364,863 | 11/1994 | Cohen et al. . |
| 5,399,574 | 3/1995 | Robertson et al. . |
| 5,434,154 | 7/1995 | Smith et al. . |
| 5,436,255 | 7/1995 | Butler .................... 514/320 |
| 5,441,969 | 8/1995 | Axelsson et al. . |
| 5,464,864 | 11/1995 | King et al. . |
| 5,466,699 | 11/1995 | Robertson et al. . |
| 5,468,768 | 11/1995 | Cipollina et al. . |
| 5,491,148 | 2/1996 | Berger et al. . |
| 5,494,910 | 2/1996 | North et al. . |
| 5,502,058 | 3/1996 | Mayer et al. . |

FOREIGN PATENT DOCUMENTS

| | | |
|---|---|---|
| 0615749 | 9/1994 | European Pat. Off. . |
| 4229805 | 3/1994 | Germany . |
| WO 94/08551 | 4/1994 | WIPO . |
| WO 94/13275 | 6/1994 | WIPO . |
| WO 95/33723 | 12/1995 | WIPO . |
| WO 96/00073 | 1/1996 | WIPO . |
| WO 96/27375 | 9/1996 | WIPO . |

OTHER PUBLICATIONS

"Intranasal Lidocaine for Treatment of Migraine", Maizeis et al., JAMA, Jul. 24/31, 1996, vol. 276, No. 4, p. 319–321.
"The Pharmacology of Current Anti–Migraine Drugs", Peroutka, Headache, Jan. 1990, vol. 30, pp. 5–11.
"Drugs and the Treatment of Migraine", Peatfield, Trends. Pharmacol. Sci., Apr. 1988, vol. 9, pp. 141–145.
"Drugs Used to Treat Migraine and Other Headaches", Drug Evaluators, American Medical Associations, 1986, 6th Edition, Chapter 13, pp. 239–252.
Dhavare, et al. "Effect of Drugs Influencing Central 5–Hydroxytryptamine Mechanisms on Amantadine–Induced Sterotyped Behaviour in the Rat", Indian Journal Physiol.Pharmacol., vol. 27 No. 1, 1983, pp. 19–24.
Maj. et al "Antagonistic Effect of Cyproheptadine on Neuroleptic–Induced Catalepsy", Pharmacology Biochemistry and Behaviour, vol. 3, No. 1, 1975, pp. 25–27.
Skuza et al., "Memantine, Amantadine, and L–Deprenyl Pontentiate the Action of L–DOPA in Monoamine–Depleted Rats", Journal of Neural Transmission, vol. 98, No. 1, 1994, pp. 57–67.
Rabey et al, "Selective Regional Effect of Various Neuroactive Drugs on Bromocriptine Concentration in the Brain of Rats", Acta Neurol. Scand., vol. 74, No. 4, 1986, pp. 289–292.
Hof et al, "Mutual Inhibition and Synergistic Effects of Ergotamine and the Calcium Antagonist Darodipine", Gen Pharmacol., vol. 17, No. 3, 1986, pp. 309–314.
Bartoli, et al "Does Lidocaine Affect Oxidative Dextromethorphan Metabolism In Vivo?", Giorn. Ital. Chim. Clin., vol. 18, No. 2, 1993, pp. 125–129.

Primary Examiner—William R.A. Jarvis
Attorney, Agent, or Firm—Dilworth & Barrese

[57] ABSTRACT

The migraine-treating effectiveness of an antimigraine drug is significantly enhanced by administering a selective 5-HT$_1$ agonist together with dextromethorphan or dextrorphan.

3 Claims, No Drawings

METHOD FOR TREATING MIGRAINE

CROSS REFERENCE TO RELATED APPLICATION

This application is a continuation-in-part of U.S. patent application Ser. No. 08/727,923, filed Oct. 9, 1996, now abandoned.

BACKGROUND OF THE INVENTION

This invention relates to a method and composition for treating migraine. More particularly, this invention is concerned with alleviating a migraine by administration of an antimigraine drug together with a nontoxic antagonist, or blocker, for the N-methyl-D-aspartate (NMDA) receptor or nontoxic substance that blocks a major intracellular consequence of NMDA receptor activation.

The term migraine is defined herein as a severe recurring headache resulting from cerebral vasoconstriction and is classified as either a classical migraine or a common migraine. See, e.g., "Remington's Pharmaceutical Sciences", 17th ed., Mack Publishing Company (1985), p. 946 and Goodman and Gilman's "The Pharmaceutical Basis Of Therapeutics", 8th ed., McGraw-Hill, Inc. (1990), pp. 944–947. A common migraine is much more likely to occur than a classical migraine. The classical migraine is associated with objective prodromal neurological signs and symptoms involving a headache that is preceded by a slowly expanding area of blindness surrounded by a sparkling edge that increases to involve up to one half of the field of vision of each eye. When the blindness clears up after approximately 20 minutes, it is often followed by a severe one-sided headache with nausea, vomiting and sensitivity to light. The common migraine is an attack without prodromal symptoms and begins as a slowly developing pain in the form of a headache that transforms into a mounting throbbing pain made worse by the slightest movement or noise. The pain is often on one side of the head only and usually occurs with nausea and sometimes vomiting.

The length of migraine is from about two hours to two days. Examples of causes of migraine are: stress related, e.g., anxiety, anger, worry, excitement, shock, depression, overexertion, changes of routine and changes of climate, food-related, e.g., chocolate, cheese and other dairy products, red wine, fried food and citrus fruits, sensory-related, e.g., bright lights or glare, loud noises and intense or penetrating smells, menstruation and contraceptive drugs.

Antimigraine drugs are well-known. See, e.g., U.S. Pat. Nos. 4,650,810, 4,914,125, 4,916,125, 4,994,483, 5,021,428, 5,200,413, 5,242,949, 5,248,684, 5,273,759, 5,317,103, 5,364,863, 5,399,574, 5,434,154, 5,441,969, 5,464,864, 5,466,699, 5,468,768, 5,491,148 and 5,494,910. Antimigraine drugs most commonly used in treatment of migraine fall into the following groups: ergot alkaloids, beta-blocking agents, calcium channel blocking agents, antidepressants, selective 5-$HT_1$ agonists (sumatriptan), sedatives, local anesthetics, adrenergic blocking agents and mixtures of these.

The antimigraine drugs have direct, or indirect effects on the 5-hydroxytryptamine (5-HT) receptor system. The 5-HT receptor system is a potent intracranial vasoconstrictor. 5-HT receptors are presently delineated into three major subclassifications—5-$HT_1$, 5-$HT_2$, and 5-$HT_3$—each of which may also be heterogeneous. The receptor mediates vasoconstriction in the carotid vascular bed and thereby modifies blood flow therein. The various classes of compounds have been proposed as 5-HT agonists or antagonists for therapeutic use of migraine, but these have not always been specific to a particular type of 5-HT receptor.

Management of migraine is complicated by the lack of a single therapy which is effective in all patients with the same migraine type and by the need to select either an abortive or prophylactic method of treatment for these migraines. Further complications involves the current use of drugs that cause dependence with extended use, such as the ergot alkaloid ergotamine. Another important consideration is that the more effective antimigraine agents in current use, e.g., the ergots, methysergide, produce severe use-limiting side effects with long term usage.

Thus, there is a need for a safe and effective drug for the treatment of migraine and related disorders which can be used either prophylactically or to alleviate an established migraine.

Heretofore, there has been no recognition or appreciation that the migraine-treating effectiveness of an antimigraine drug can be appreciably enhanced, or potentiated, by coadministration of this drug with an NMDA receptor antagonist or substance that blocks a major intracellular consequence of NMDA receptor activation.

SUMMARY OF THE INVENTION

In accordance with the present invention, a method of alleviating a migraine is provided which comprises coadministering to a mammal exhibiting a migraine (a) a migraine-treating amount of an antimigraine drug and (b) an antimigraine-potentiating amount of at least one member of the group consisting of nontoxic antagonist for the NMDA receptor and nontoxic substance that blocks a major intracellular consequence of NMDA receptor activation.

Further in accordance with this invention, a composition for alleviating migraine is provided which comprises (a) a migraine-treating amount of an antimigraine drug selected from the group consisting of ergot alkaloids, beta-blocking agents, calcium channel blocking agents, antidepressants, selective 5-$HT_1$ agonists (sumatriptan etc.), sedatives and adrenergic blocking agents and (b) an antimigraine-potentiating amount of at least one member of the group consisting of nontoxic antagonist for the NMDA receptor and nontoxic substance that blocks a major intracellular consequence of NMDA receptor activation.

The expression "N-methyl-D-aspartate receptor" shall be understood to include all of the binding site subcategories associated with the NMDA receptor, e.g., the glycine-binding site, the phenylcyclidine (PCP)-binding site, etc., as well as the NMDA channel. Thus, the invention herein contemplates the use of nontoxic substances that block an NMDA receptor binding site, e.g., dextrorphan, or the NMDA channel, e.g., a source of magnesium such as magnesium sulfate.

The term "nontoxic" as used herein shall be understood in a relative sense and is intended to designate any substance that has been approved by the United States Food and Drug Administration ("FDA") for administration to humans or, in keeping with established regulatory criteria and practice, is susceptible to approval by the FDA for administration to humans. The term "nontoxic" is also used herein to distinguish the NMDA receptor antagonists, or blockers, that are useful in the practice of the present invention from NMDA receptor antagonists such as MK 801 (the compound 5-methyl-10,11-dihydro-SH-dibenze[a,d] cyclohepten-5,10-imine), CPP (the compound 3-[2-carboxypiperazin-4-yl] propyl-1-phosphoric acid) and PCP (the compound 1-(1-phenylcyclohexyl)piperidine) whose toxicities effectively preclude their therapeutic use.

The expression "antimigraine drug" as used herein shall be understood to mean a drug which is effective to either prevent or inhibit the onset of a migraine and/or to alleviate one or more symptoms of a migraine, in particular, the pain which is associated with this condition.

DESCRIPTION OF THE PREFERRED EMBODIMENTS

Any of the antimigraine drugs can be used herein. For extensive listings of antimigraine drugs, see, e.g., Goodman and Gilman's "The Pharmaceutical Basis of Therapeutics" and "Remington's Pharmaceutical Sciences" both of which as referred to above. Additional antimigraine drugs are listed in the U.S. Pat. Nos. as stated hereinabove, the contents of which are incorporated by reference herein. Specific antimigraine drugs that can be used herein include ergot alkaloids such as ergotamine tartrate, dihydroergotamine mesylate, methysergide maleate, methylergonovine maleate, ergoloid mesylates, bromocriptine mesylates and ergonovine maleate, beta-blocking agents such as propranolol, atenolol, alprenolol, timolol, metoprolol, labetolol, pindolol, oxprenolol and nadolol, calcium channel blocking agents such as flunarizine, cinnarizine, nimodipine, nifedipine, cyproheptadine, diltiazem and verapamil hydrochloride, antidepressants such as amitriptyline hydrochloride, imipramine, desipramine, doxepin, protriptyline, phenelzine, isocarboxazide and lithium carbonate, selective 5-HT$_1$ agonists such as sumatriptan, sedatives such as butalbital and meprobamate, local anesthetics such as lidocaine, bupivacaine, chloroprocaine, dibucaine, etidocaine, isobucane, mepivacaine, meprylcain, piperocaine, prilocaine, procaine, tetracaine, propoxycaine, primacaine, parethoxycaine, pyrrocaine, proparacaine and their pharmaceutically acceptable salts and adrenergic blocking agents such as ergotamine and dihydroergotamine.

Among the nontoxic substances that block the NMDA receptor and as such are useful for potentiating the migraine-treating activity of an antimigraine drug in accordance with this invention are dextromethorphan ((+)-3-hydroxy-N-methylmorphinan), and its metabolite dextrorphan ((+)-3-hydroxy-N-methylmorphinan), their mixtures and their pharmaceutically acceptable salts. Other useful nontoxic substances that block the NMDA receptor include amantadine (1-aminoadamantine), memantine (3,5 dimethylaminoadamantone), pyrroloquinoline quinone and cis-4-(phosphonomethyl)-2-piperidinecarboxylic acid, their mixtures and their pharmaceutically acceptable salts. Of the NMDA receptor antagonists,.dextromethorphan in the form of its hydrobromide salt is preferred for use herein due to its high degree of proven safety and its ready availability. While dextrorphan and its pharmaceutically acceptable salts will also provide excellent results, it is not known to be in commercial manufacture at this time.

In addition to, or in place of, a blocker for the NMDA receptor, at least one nontoxic substance that blocks a major intracellular consequence of NMDA receptor activation can also be used to potentiate an antimigraine drug in accordance with the invention. Activation of the NMDA receptor, a subtype of excitatory amino acid receptors, induces a number of changes in the functional activity of nerve cells and, in particular, their capacity for excitability or inhibition in the presence of an addictive substance via an increase in intracellular Ca++ concentration. The major consequences of NMDA receptor activation include the following sequences, or cascades, of events occurring within nerve cells:

a) translocation and activation of protein kinases such as protein kinase C→phosphorylation of substrate proteins such as cytosolic enzymes, channel proteins, receptor proteins, etc.→changes in functional activity;

b) initiation of early gene (c-fos, c-jun, zif-268, etc.) expression by either increased intracellular Ca++ or Ca++-activated protein kinases→expression of functional genes responsible for production of cellular enzymes (such as protein kinases), receptor proteins (such as the NMDA receptor), ion channel proteins (such as K+, Na+, Ca++ channels), neuropeptides (such as dynorphin), etc.→changes in functional activity;

c) Ca++/calmodulin (or other Ca++ binding proteins) induced activation of enzymes and other cellular components→activation of Ca++/calmodulin-protein kinase systems such as Ca++/calmodulin kinase II→autophosphorylation of enzymes (e.g., Ca++/calmodulin kinase II) or other functional proteins→changes in functional activity;

d) Ca++/calmodulin induced activation of constitutive nitric oxide synthase as well as induction of inducible nitric oxide synthase→production of nitric oxide→i) production of cyclic guanosine monophosphate via activation of guanosine cyclase resulting in activation of protein kinases and early gene expression; ii) direct protein modification such as enzymes, receptor and/or channel proteins; iii) lipid membrane modification and/or nucleic acid modification via scavenge of free radicals; iv) induction of neurotoxicity at higher nitric oxide levels; v) retrograde actions in adjacent neurons or glial cells such as facilitation of glutamate release/NMDA receptor activation and/or inhibition of post-synaptic NMDA receptors→changes in functional activity;

e) interactions with the cyclic adenosine monophosphate/protein kinase A system, the phospholipase C-inositol triphosphate-Ca++/diacylglycerol-protein kinase system, the phospholipase A2-arachidonic acid/prostanoids/leukotrienes system→changes in functional activity induced by second messenger systems other than NMDA receptor/Ca$^{++}$/Ca$^{++}$-calmodulin/protein kinase systems; and, f) interactions with other excitatory amino acid receptor subtypes including non-NMDA receptors and metabotropic receptors as well as intracellular events subsequent to the activation of these excitatory amino acid receptor subtypes→changes in functional activity induced by the non-NMDA and metabotropic receptor activation.

A substance that blocks the NMDA receptor will effectively prevent all of the foregoing major intracellular sequences of events from taking place. However, even with activation of the NMDA receptor, it is still possible to treat migraine in accordance with this invention by administering the antimigraine drug and a substance that blocks at least one of the foregoing major intracellular sequences of events. Thus, e.g., a substance that interferes with translocation and activation of protein kinase C or with calmodulin induced activation of constitutive nitric oxide synthase as well as induction of inducible nitric oxide synthase is also useful for the practice of this invention. Nontoxic substances that block a major intracellular consequence of NMDA receptor activation and are therefore useful in the practice of the invention include inhibitors of protein kinase C, e.g., gangliosides such as ganglioside GM$_1$ (monosialoganglioside) and ganglioside GT$_{1b}$ (trisialoganglioside); amphipathic long chain bases such as sphingosine, N,N,N-trimethylsphingosine, sphinganine and psychosine;

quinolyloxazole-2-ones such as 4-methyl-5-(3-quinolinyl)-2-(3H)-oxazolone and phenyl-5-(2-quinolinyl)-2-3(3H)-oxazolone; 1,4-bis-(amino-hydroxyalkylamino)-anthraquinones such as 1,4-bis-(3-propylamino-2-hydroxypropylamino)-9,10 anthracenedione and 1,4-bis-(3-benzylamino-2-hydroxypropylamino)-9,10 anthracenedione; and, mixtures and pharmaceutically acceptable salts of any of the foregoing.

Additional nontoxic substances that block a major intracellular consequence of NMDA receptor activation and as such are useful in the practice of the invention include inhibitors of calmodulin such as the phenothiazines, in particular, chlorpromazine, chlorpromazine sulfoxide, prochlorperazine dimaleate, perphenazine, trifluoperazine, fluphenazine, fluphenazine enanthate, fluphenazine decanoate, thioridazine, mesoridazine besylate, piperacetazine, acetophenazine dimaleate, carphenazine dimaleate, butaperazine dimaleate and phenothiazine sulfoxide; naphthalenesulfonamides such as N-(6-aminohexyl)-5-chloro-1-naphthalenesulfonamide, N-(6-aminohexyl)-5-chloro-2-naphthalenesulfonamide and N-(6-aminohexyl)-5-bromo-2-naphthalenesulfonamide; 4-substituted-4H,6H-pyrrolo[1,2-a][4,1] benzoxazepines such as 1,3-dihydro-1-{1-[(4-methyl-4H,6H-pyrrolo[1,2-a][4,1] benzoxazepin-4-yl)methyl]-4-piperidinyl}-2H-benzimidazole-2-one; benzhydryls such as N-[2](diphenylmethylthioethyl]-2-(trifluoromethyl)-benzeneethanamine, N-[2-(bis(4-fluorophenyl)methylthio)-ethyl]-2-(trifluoromethyl)benzeneethanamine and N-[2-(bis(4-fluorophenyl)methylthio)ethyl]-3-(trifluoromethyl)benzene-ethanamine; tricyclic antidepressant drugs such as imipramine, 2-chloroimipramine and amitriptyline; penfluridol; haloperidol; pimozide; clozapine; calmidazolin; and, mixtures and pharmaceutically acceptable salts of any of the foregoing.

Of the two groups, the NMDA-receptor antagonists are preferred and of these, dextromethorphan is especially preferred for the reason previously stated.

With regard to dosage levels, the antimigraine drug must be present in a migraine-treating amount, e.g., at a level corresponding to the generally recommended adult human dosages for the antimigraine drug, and the NMDA receptor blocker or substance that blocks a major intracellular consequence of NMDA activation must be present at a level that potentiates the migraine-treating effectiveness of the antimigraine drug. Specific dosage levels for the migraine-treating drug that can be used herein as given, inter alia, in the "Physicians' Desk Reference", 1996 Edition (Medical Economics Data Production Company, Montvale, N.J.) as well as in other reference works including Goodman and Gilman's "The Pharmaceutical Basis of Therapeutics" and "Remington's Pharmaceutical Sciences" both of which as referred to above. Given the wide variations in dosage level of the antimigraine drug which depends to a large extent on the specific antimigraine drug being administered, there can similarly be a wide variation in the dosage level of the NMDA receptor blocker or substance that blocks a major intracellular consequence of NMDA receptor activation. These amounts can be determined for a particular drug combination in accordance with this invention employing routine experimental testing.

By administering the antimigraine drug in combination with the NMDA receptor blocker or substance that blocks a major intracellular consequence of NMDA activation, this will significantly enhance the duration of migraine relief than with the antimigraine drug administered by itself, e.g., an increase of 50% to 100% and even greater in many cases. All modes of administration are contemplated, e.g., administration can be orally, rectally, parenterally, intranasally, topically, or by intravenous, intramuscular, subcutaneous or intracerebro-ventricular injection or in a form suitable for administration by inhalation or insufflation. The formulations may, where appropriate, be conveniently presented in discrete dosage units and may be prepared by any of the methods well known in the art of pharmacy.

A therapeutic composition containing the antimigraine drug and nontoxic NMDA receptor antagonist or nontoxic substance that blocks a major intracellular consequence of NMDA receptor activation will ordinarily be formulated with one or more pharmaceutically acceptable ingredients in accordance with known and established practice. Thus, the composition can be formulated as a liquid, powder, elixir, injectable solution, etc. Formulations for oral use can be provided as tablets or hard capsules wherein the pharmacologically active ingredients are mixed with an inert solid diluent such as calcium carbonate, calcium phosphate or kaolin, or as soft gelatin capsules wherein the active ingredients are mixed with an oleaginous medium, e.g., liquid paraffin or olive oil.

For topical administration in the mouth, the pharmaceutical compositions may take the form of buccal or sublingual tablets, drops or lozenges formulated in conventional manner.

For topical administration to the epidermis the compounds of the invention may be formulated as creams, gels, ointments or lotions or as transdermal patches. Such compositions may, for example, be formulated with an aqueous or oily base with the addition of suitable thickening, gelling, emulsifying, stabilizing, dispersing, suspending, and/or coloring agents.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage from e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas. e.g. containing conventional suppository bases such as cocoa butter or other glyceride.

For intranasal administration the compounds of the invention may be used, for example, as a liquid spray, as a powder or in the form of drops.

For administration by inhalation the compounds according to the invention are conveniently delivered in the form of an aerosol spray presentation from pressurized packs or a nebulizer, with the use of a suitable propellant, e.g. dichlorodifluoromethane, trichlorofluoromethane, dichlorotetrafluoroethane, tetrafluoroethane, heptafluoropropane, carbon dioxide or other suitable gas. In the case of a pressurized aerosol the dosage unit may be determined by providing a valve to deliver a metered amount. Capsules and cartridges of e.g. gelatin for use in an inhaler or insulator may be formulated containing a powder mix of a compound of the invention and a suitable powder base such as lactose or starch.

Aqueous suspensions can include pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethyleneoxycetanol, or condensation products of ethylene oxide with partial esters derived from fatty acids and a hexitol, e.g., polyoxyethylene sorbitol monooleate or condensation products of ethylene oxide with partial esters derived from fatty acids and hexitol anhydrides, e.g., polyoxyethylene sorbitan monoleate. The aqueous suspensions can also contain one or more preservatives, e.g., ethyl-or-n-propyl-p-hydroxy benzoate, one or more coloring agents, one or more flavoring agents and one or more sweetening agents, such as sucrose, saccharin or sodium or calcium cyclamate.

If desired, the antimigraine drug and antimigraine-potentiating amount of an NMDA receptor blocker or substance that blocks a major intracellular consequence of NMDA receptor activation can be combined with one or more drug or drug combinations to provide relief of migraine. See for example, Peatfield, "Drugs and the Treatment of Migraine", Trends. Pharmacol. Sci., 1988, Vol. 9, pp. 141–145, Drug Evaluators, "Drugs Used to Treat Migraine and other Headaches", American Medical Association, 1986, 6th Ed., pp: 239–263 and Peroutka, "The Pharmacology of Current Anti-Migraine Drugs", Headache, 1990, 30:5–11.

Thus, in addition to the antimigraine drug and antimigraine-potentiating amount of an NMDA receptor blocker or substance that blocks a major intracellular consequence of NMDA receptor activation, the therapeutic composition herein can contain at least one other pharmacologically active substance e.g., caffeine (a stimulant), an antiemetic drug such as metoclopramide, domperidone, belladonna alkaloids and phenothiazines such as chlorpromazine, prochlorperazine, and promethazine, a nonnarcotic analgesic, e.g., acetaminophen or a nonsteroidal anti-inflammatory drug such as aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, nabumetone, naproxen, oxaprozin, phenylbutazone, piroxicam, sulindac, tolmetin, zomepirac, and the like.

EXAMPLES 1–25

The following unit dosage forms are illustrative of the migraine-treating drug combinations in accordance with the present invention:

| Example | Dosage Form | Antimigraine Drug (mg) | NMDA Receptor Blocker (mg) | Additional Active Component(s) (mg) |
|---|---|---|---|---|
| 1 | tablet | ergotamine tartrate (1) | dextromethorphan hydrobromide (30) | caffeine (100) |
| 2 | tablet | ergotamine tartrate (.3) | dextromethorphan hydrobromide (30) | phenobarbital (20) |
| 3 | tablet | methysergide (1) | dextromethorphan hydrobromide (30) | caffeine (100) |
| 4 | tablet | ergotamine tartrate (1) | dextromethorphan hydrobromide (30) | caffeine (100) pentobarbital sodium (30) |
| 5 | tablet | butalbital (50) | dextromethorphan hydrobromide (30) | aspirin (650) |
| 6 | tablet | butalbital (50) | dextromethorphan hydrobromide (30) | caffeine (40); acetaminophen (325) |
| 7 | capsule or tablet | butalbital (50) | dextromethorphan hydrobromide (30) | caffeine (40); aspirin (325) |
| 8 | suppository | ergotamine tartrate (2) | dextromethorphan hydrobromide (30) | caffeine (100) |
| 9 | suppository | ergotamine tartrate (2) | dextromethorphan hydrobromide (30) | caffeine (100); pentobarbital (60) |
| 10 | intramuscular injection | dihydroergotamine mesylate (1 mg/ml) | dextromethorphan hydrobromide (30) | |
| 11 | intravenous injection | dihydroergotamine mesylate (2 mg/ml) | dextromethorphan hydrobromide (30) | |
| 12 | inhalation | ergotamine tartrate (.36) | dextromethorphan hydrobromide (30) | |
| 13 | suppository | methysergide (2) | dextromethorphan hydrobromide (30) | caffeine (100) |
| 14 | tablet | propranolol hydrochloride (10) | dextromethorphan hydrobromide (30) | |
| 15 | tablet | propranolol hydrochloride (40) | dextromethorphan hydrobromide (30) | |
| 16 | intravenous injection | dihydroergotamine mesylate (.5) | dextromethorphan hydrobromide (30) | metoclopramide (10) |
| 17 | tablet | verapamil hydrochloride (80) | dextromethorphan hydrobromide (30) | |
| 18 | injection | sumatriptan (6) | dextromethorphan hydrobromide (30) | sodium chloride (3.5) |

-continued

| Example | Dosage Form | Antimigraine Drug (mg) | NMDA Receptor Blocker (mg) | Additional Active Component(s) (mg) |
|---|---|---|---|---|
| 19 | tablet | amitriptyline hydrochloride (25) | dextromethorphan hydrobromide (30) | |
| 20 | tablet | ergonovine maleate (.2) | dextromethorphan hydrobromide (30) | |
| 21 | tablet | ergotamine tartrate (1) | amantadine (60) hydrochloride | |
| 22 | tablet | ergotamine tartrate (1) | memantine (60) hydrochloride | |
| 23 | injection | sumatriptan (6) | amantadine (60) hydrochloride | |
| 24 | injection | sumatriptan (6) | memantine (60) hydrochloride | |
| 25 | tablet | amitriptyline hydrochloride (25) | amantadine (60) hydrochloride | |

EXAMPLES 26–28

Intranasal drops and sprays are especially advantageous dosage forms for administering local anesthetics as the antimigraine drug. Suitable formulations include the following:

| Example | Components |
|---|---|
| 26 | lidocaine hydrochloride (4 g); dextromethorphan hydrobromide (1 g); methylcellulose (0.25 g); sodium chloride (0.9 g); water, purified (100 ml). |
| 27 | lidocaine hydrochloride (4 g); amantadine hydrochloride (2 g); methylcellulose (0.25 g); sodium chloride (0.9 g); water, purified (100 ml). |
| 28 | lidocaine hydrochloride (4 g); memantine hydrochloride (2 g); methylcellulose (0.25 g); sodium chloride (0.9 g); water, purified (100 ml). |

In each of these unit doses, the NMDA receptor antagonist dextromethorphan hydrobromide significantly enhances the migraine-treating activity of the antimigraine component.

What is claimed is:

1. A method of alleviating a migraine which comprises coadministering to a mammal exhibiting a migraine (a) a migraine-treating amount of a selective 5-$HT_1$ agonist and (b) an antimigraine-potentiating amount of at least one member of the group consisting of dextromethorphan, dextrorphan and pharmaceutically acceptable salt thereof.

2. The method of claim 1 wherein the selective 5-$HT_1$ agonist is sumatriptan.

3. The method of claim 1 wherein (a) and (b) are coadministered as a sustained release dosage form.

* * * * *